(12) United States Patent
Taboada et al.

(10) Patent No.: US 8,403,918 B2
(45) Date of Patent: Mar. 26, 2013

(54) AUTOMATED NON-INVASIVE CAPSULECTOMY AND ANTERIOR SEGMENT SURGICAL APPARATUS AND METHOD

(76) Inventors: John Taboada, San Antonio, TX (US); John M. Taboada, San Antonio, TX (US); David C. Brown, Fort Myers, FL (US)

(*) Notice: Subject to any disclaimer, the term of this patent is extended or adjusted under 35 U.S.C. 154(b) by 454 days.

(21) Appl. No.: 12/752,909

(22) Filed: Apr. 1, 2010

(65) Prior Publication Data

US 2011/0245814 A1 Oct. 6, 2011

(51) Int. Cl.
A61B 18/18 (2006.01)
A61B 19/00 (2006.01)
(52) U.S. Cl. .......................... 606/4; 128/898
(58) Field of Classification Search .......... 606/4–6; 128/898
See application file for complete search history.

(56) References Cited

U.S. PATENT DOCUMENTS

| | | | |
|---|---|---|---|
| 5,738,676 A | 4/1998 | Hammer et al. | |
| 7,467,869 B2 | 12/2008 | Kahlen | |
| 7,575,322 B2 | 8/2009 | Somani | |
| 7,652,761 B2 | 1/2010 | Somani et al. | |
| 2001/0045529 A1* | 11/2001 | Iketaki et al. | 250/493.1 |
| 2003/0039293 A1* | 2/2003 | Scheps | 372/69 |
| 2006/0004347 A1 | 1/2006 | Altshuler et al. | |
| 2006/0100613 A1* | 5/2006 | McArdle et al. | 606/4 |
| 2006/0195076 A1 | 8/2006 | Blumenkranz | |
| 2008/0281303 A1 | 11/2008 | Culbertson et al. | |
| 2008/0281413 A1 | 11/2008 | Culbertson et al. | |
| 2009/0012507 A1 | 1/2009 | Culbertson et al. | |
| 2010/0079853 A1* | 4/2010 | Rakich et al. | 359/334 |

FOREIGN PATENT DOCUMENTS

| | | |
|---|---|---|
| JP | 2009535099 | 10/2009 |
| WO | WO2006074469 | 7/2006 |
| WO | WO2007084694 | 7/2007 |
| WO | WO 2008055506 A2 * | 5/2008 |
| WO | WO2009033110 | 3/2009 |
| WO | WO2009039302 | 3/2009 |

OTHER PUBLICATIONS

Am Intra-ocular Implant Soc J, vol. 7, p. 332, 1981.
Am Intra-ocular Implant Soc J, vol. 8, 1982.
Rev of Ophthalmology, Oct. 2009, p. 29.
"Laboratory Science: Visualization of Femtosecond Laser Pulse-Induced Microincisions Inside Crystalline Lens Tissue." vol. 35, p. 1979-1983, Nov. 2009.
"ELM: Home Built Laser Projector" p. 1-16, Oct. 2004.

* cited by examiner

*Primary Examiner* — Dawayne A Pinkney
(74) *Attorney, Agent, or Firm* — Claude E. Cooke, Jr.; Cooke Law Firm

(57) ABSTRACT

An economical computer-controlled non-invasive laser apparatus and method to perform anterior segment surgery in an eye are disclosed. The laser source may include a pumping laser, a Nd:YAG laser cavity gain media, a stimulated Raman converter crystal, intracavity beam diameter-reducing optics, and an intracavity Q-switching crystal. The laser pulses have a selected wavelength for anterior segment surgery. A laser pulse delivery and treatment control mechanism and method for the practicing surgeon are also provided. The laser pulses and delivery system may be used in anterior segment surgery for cataracts, where the laser pulses may be used to form the capsulotomy, to form the corneal incision or to disintegrate contents of the capsule before removal. The laser and delivery system may also the used to treat a capsule and lens for correcting or preventing presbyopia and to treat a cornea to correct visual deficiencies in an eye.

28 Claims, 2 Drawing Sheets

AUTOMATED NON-INVASIVE CAPSULECTOMY AND ANTERIOR SEGMENT SURGICAL APPARATUS AND METHOD

BACKGROUND OF INVENTION

1. Field of the Invention

The present invention relates to an anterior segment surgical apparatus in ocular surgery, and more particularly to a laser apparatus having application in cataract surgery for capsulorhexis, i.e. the cutting of a capsulotomy in the anterior capsule of a lens of an eye, and for other procedures in cataract surgery. The apparatus may also be used in surgical procedures for the cornea and posterior capsule.

2. Description of Related Art

The standard procedure for correcting vision loss due to cataracts is to remove the natural lens and to replace it with a prosthetic lens. In typical cataract surgery, an initial incision is made into the cornea of the eye and then the surgeon creates a circular opening in the anterior lens capsule. This is referred to as a capsulotomy. Producing the circular opening is often a critically demanding procedure. It is also known as an anterior lens capsulectomy once the circular fragment of the lens capsule is removed. The latter name is in reference to the analogous posterior lens capsulotomy, which has come to be well known in surgery practice and which involves the use of a pulsed YAG laser. Once the anterior capsulotomy is completed, the natural lens cortex is extracted by breaking it up into small pieces, which are drawn through the initial opening. As this procedure and pseudophakic materials have improved over time, the initial incision has become smaller, such that it is now normally less than 3 mm. Reducing the initial incision has improved the surgical outcome but has placed higher and higher demands on the surgeon and the surgical instruments that pass through the initial incision.

The anterior capsulotomy portion of cataract surgery as defined above preferably results in a circular opening of a selected diameter and without radial tears. Ideally, it has smooth edges. The usual instruments used by the surgeon are the cystotome or forceps, which are used to basically puncture and tear the capsule tissue to produce the opening. The results are at best imperfect circles, and sometimes radial tears or other adverse events occur. For advanced lens technologies, it is particularly important to consistently produce a smooth, intact and round capsulotomy without radial tears in the capsule.

Laser techniques that have been attempted include the application of the well established posterior capsulotomy YAG laser operating with a 1064 nm wavelength. In 1981, Aron-Rosa reported on laser opening of the anterior capsule from 1 to 24 hours before extra-capsular cataract surgery. (Am Intra-ocular Implant Soc J, Vol 7, p. 332, 1981) It was shown that by depositing one laser pulse at a time aimed at the anterior lens capsule, a rudimentary capsulectomy could be produced, but with complications in some cases. The complications included high intraocular pressures caused by the laser pulse shock wave, edge roughness and irregular shaped capsulectomies. Unintended exposure of the retina to hazardous levels of laser radiation can occur if the pulse is not blocked by a necessary plasma breakdown process at the focal point at the lens anterior capsule. Other disadvantages include the tedium of depositing a few hundred pulses, one pulse at a time, a situation that can contribute to operator error. For these reasons, such a technique has not been accepted by surgeons.

In 1982, Horn et al reported on the use of a "cool" laser operating at a 1220 nm wavelength. (Am Intra-ocular Implant Soc J, Vol 8, 1982) The intended objective of moving from the 1064 nm wavelength to the 1220 nm wavelength was to cut power requirements 100-fold and avoid jeopardizing the retina when doing anterior chamber surgical treatments. Horn et al used a very elaborate laser system to achieve the preferred wavelength: a Nd:YAG pump laser source was converted to 532 nm, which was then used to pump a 600 nm dye laser, and finally converted to a 1220 nm laser source by means of a high-pressure hydrogen gas cell. The work was done on rabbit subjects. No report of follow-on work was found.

Various reports of the use of lasers in cataract surgery have appeared in more recent years. In 2009, a LenSx femtosecond laser received approval from the U.S. Food and Drug Administration for creation of the capsulorhexis during cataract surgery. (Rev of Ophthalmology, October 2009, p. 29) A recent patent application by the same company discussed the use of a pulsed laser for: photodisruption of a portion of a targeted region in the lens of an eye, for making an incision in the capsule of the lens and for making an incision in the cornea of the eye (WO 2009/039302 A2). These lasers normally emit at wavelengths shorter than 1000 nm, which raises their potential of affecting the sensitive retina. The femtosecond lasers are also expensive and require substantial maintenance.

What is needed is a pulsed laser system that can be used to form the capsulorhexis during cataract surgery that is effective and economical, so that it can be made widely available for use by surgeons, and that employs a wavelength having preferred absorption properties in the tissue of an eye.

BRIEF SUMMARY OF THE INVENTION

The present invention substantially eliminates the above mentioned problems associated with the practice of the prior art and provides an economical, automated non-invasive capsulectomy instrument and method. The invention makes novel use of a selected wavelength in the laser spectrum to reduce the required pulse energy and to produce a fine excision on the lens anterior capsule. To accomplish the generation of effective laser pulses, a laser cavity is disclosed, which may be pumped by two solid state laser diodes, that contains a gain medium, a Raman crystal, either Q-switching or a mode-locking device to generate a train of selected wavelength near-IR laser pulses and necessary optics. Also disclosed is a compact and economical laser pulse delivery system, automated to produce reliable pre-programmed capsulectomies or other anterior segment surgical treatments using computer-controlled pattern generation, which may be used to designate the treatment loci and deliver the laser pulses to the capsule, cornea, or lens of an eye. In some embodiments, computer-controlled beam focus, through-the-optical-axis computer-controlled azimuth angle articulator, computer-controlled elevation angle articulator, dichroic beam splitter and treatment beam director with automated eye tracking, contact lens, operator viewing microscope and operator programmable control computer may be provided. Method for use of the apparatus by a surgeon to form a capsulectomy, which may be formed before an incision in the cornea is made (i.e., be non-invasive), to photodisrupt a lens prior to its removal, to make an incision in a cornea and to treat a cornea to improve vision are also disclosed.

BRIEF DESCRIPTION OF THE DRAWINGS

The invention will be more fully understood from the following detailed description of representative embodiments thereof read in conjunction with the accompanying drawings wherein.

DETAILED DESCRIPTION OF THE INVENTION

Figure 1:
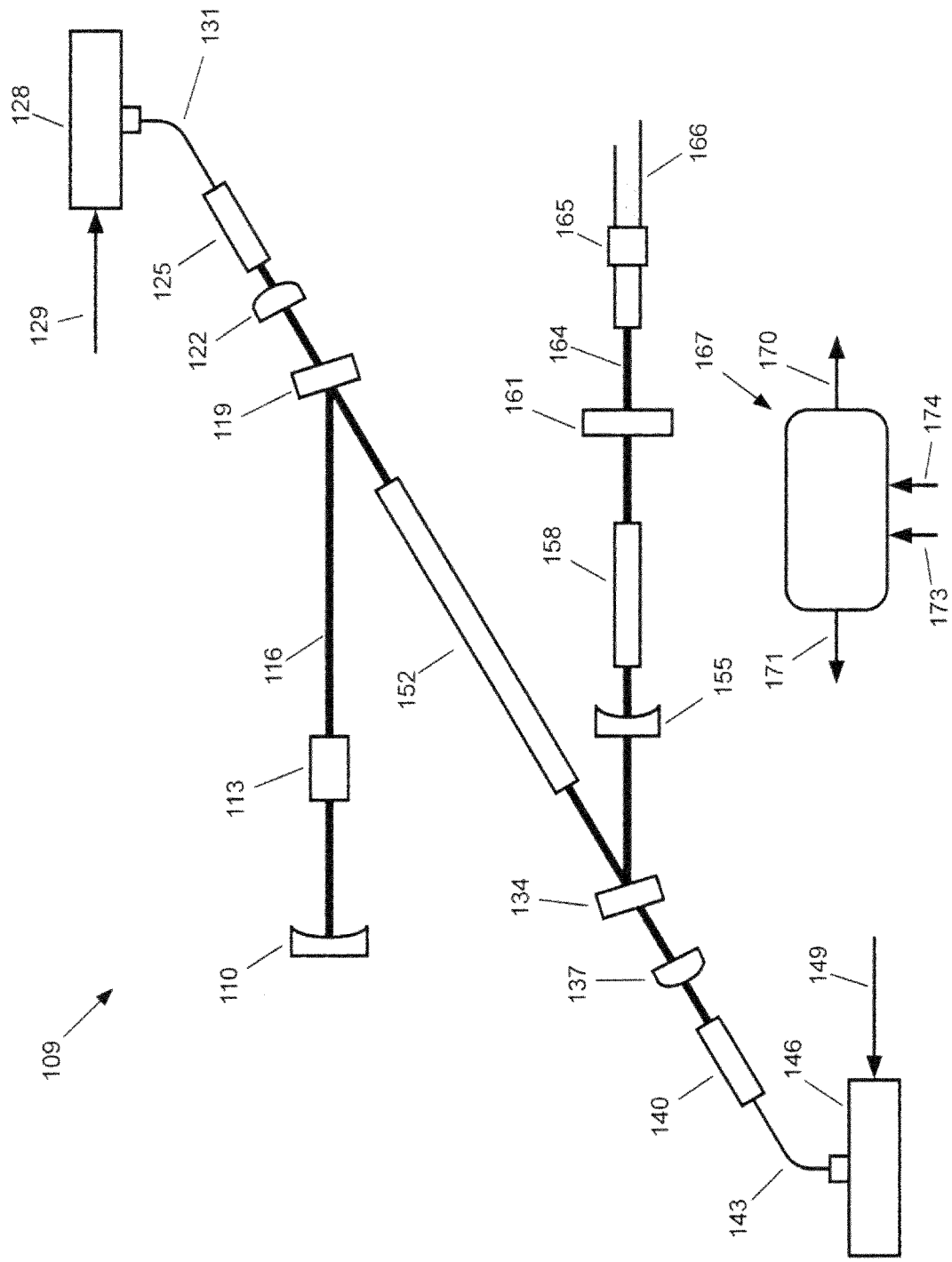
FIG. 1 is a schematic of the component parts of the laser system of the invention.

Referring now to the drawings, FIG. 1 shows a schematic layout of laser system 109 of the invention. The function of the laser system is to produce a train of pulses emanating as 166 with sufficient energy to incise capsular tissue. The wavelength of the laser pulse generated by the laser system 109 is selected by considering the absorptive properties of the ocular region and the target tissue. Since most of the ocular media is water, the ideal wavelength of the laser source for ocular capsulectomy is one where water has a selected absorption characteristic; that is, the absorption is not too high or too low. This occurs toward the UV end of the spectrum as well as toward the IR end. The UV end is complicated by sharp absorption discontinuities from corneal regions to aqueous regions. The IR region, on the other hand, progresses smoothly to high absorption, becoming opaque at 1400 nm. The optimum absorption lies between 1064 nm and 1400 nm. To derive an estimate of optimum absorption, Beer's Law for light absorption may be used:

$$I=I_0 e^{-\alpha \cdot x}, \quad (\text{Eq. 1})$$

where I is the intensity, power or energy in a beam of initial intensity $I_0$ at depth x into a media having an absorption coefficient $\alpha$. The energy deposited $E_d$ in a short distance $x_1$ to $x_2$ at a depth $x_1$ into the media can be expressed as $$E_d = E_0 e^{-\alpha \cdot x_1}(1-e^{-\alpha \cdot x_2}) \quad (\text{Eq. 2})$$

There is an absorption coefficient where $E_d$ is at its maximum, which may be determined by solving $$\frac{dE_d}{d\alpha} = \frac{d}{d\alpha}[e^{-\alpha \cdot x_1}(1-e^{-\alpha \cdot x_2})] = 0, \quad (\text{Eq. 3})$$

which yields $$\alpha = \frac{1}{x_2}\ln\left(\frac{x_1}{x_1+x_2}\right) \quad (\text{Eq. 4})$$

For lens surgery at the anterior capsule, $x_1$ can be chosen to be 0.36 cm and $x_2$ approximately 0.37 cm. This results in $$\alpha = -1.873 \text{ cm}^{-1}$$

A similar value for the target plane being the posterior capsule yields $$\alpha = 0.912 \text{ cm}^{-1}$$

A preferable absorption coefficient should, therefore, lie between these two values. To determine what wavelengths produce these absorption coefficients in water (which is the major portion of the clear ocular tissue) reference is made to published measurements, for example: K. F. Palmer and D. William, "Optical properties of water in the near infrared," J. Opt. Soc. Am., 1107-1110, 1974. The primary Nd:YAG 1064 nm wavelength, for example, has an absorption coefficient of 0.154 cm$^{-1}$ in water. This is definitely under-absorbing for targets at the lens capsule, posterior and anterior. The corresponding wavelengths for the above derived absorption coefficients in water based on the data by Palmer and William are 1300 nm for the anterior capsule and about 1150 nm for the posterior capsule. If such a laser source can be found that operates at a wavelength somewhat above 1150 nm and preferably below 1300 nm, the disclosed laser instrument can be advantageously applied to capsulectomies in the anterior and posterior capsule. Since in the present invention the beam is not focused anterior to the lens capsule no harm will be done to anterior tissues and the process can be referred to as being non-invasive. There is limited concern with retinal exposure because the aqueous absorption at 1197 nm is much higher than it is at 800 nm to 1100 nm. Further, since the composition of the lens capsule is high in lipids, it would be advantageous to target wavelengths close to 1200 nm, which is close to a peak lipid absorption band.

We have invented an efficient embodiment of such a laser source, and it is obtained by a stimulated Raman-shift process acting on a laser gain crystal, such as a Nd:YAG crystal or a crystal that may be in the same family, such as Nd:VNO$_4$ (neodymium vanadate). The laser gain crystal will be referred to as Nd:YAG in this discussion. The laser gain crystal preferably has a gain greater than 1%, and more preferably greater than 50%. Referring to FIG. 1, we disclose an optical arrangement including Raman crystal 158, which may be barium nitrate, serving as the wavelength converter embedded in a laser cavity. A barium nitrate crystal, when pumped by 1064 nm Q-switched or mode-locked laser pulses, will generate 1197 nm wavelength Raman-shifted laser pulses, which are at a wavelength in the range of preferred wavelengths for capsulectomies and other surgical procedures in the anterior segment of an eye. Other Raman crystals may be used, being selected to produce a wavelength in the preferred range of wavelengths by Raman shifting the wavelength produced by the laser gain crystal, and having a gain preferably greater than 1% and more preferably having a gain greater than 50%.

The cavity of laser system 109 is formed by high-reflectivity mirrors 110, 119 and 134, which reflect both 1064 nm and 1197 nm wavelengths, and mirror 161, which partially transmits the 1197 nm wavelength but highly reflects at the 1064 nm wavelength of the YAG crystal. The folded arrangement for the laser cavity of laser system 109 allows for the efficient optical pumping of Nd:YAG laser crystal 152 by coupling the emission of pump lasers, which may be two solid state diode lasers emitting at 808 nm. Pump lasers 128 and 146 with corresponding power supplies (not shown) may be coupled to the cavity by fiber optic couplings 131 and 143, coupling lenses 125 and 140 and coupling lenses 122 and 137, respectively. Fiber optic couplings 143 and 131 convey the pump radiation to coupling lenses 140, 137 and 125, 122. These optical elements couple the pump 808 nm optical radiation through cavity reflectors 134 and 119 to the respective ends of Nd:YAG laser gain crystal 152. Preferably, two pump lasers are used, although one may be used. Cavity laser reflectors 134 and 119, in addition to having high reflectivity at 1064 nm and 1197 nm, have high transmissivity at the 808 nm pump wavelength, which allows the pump light to pass through. The cavity of laser system 109 may be further refined to enhance the efficiency of the Raman conversion process by giving end reflector 110 a concave curvature and adding lens 155 so as to form a contracting or beam-reducing telescope, reducing the beam diameter passing through the Raman crystal 158 to a selected distribution and thereby increasing the power density and, as a result, increasing the conversion efficiency. The laser cavity of laser system 109 can be modulated to produce Q-switched or mode locked pulses by incorporating a saturable absorber or an acousto-optic modulator as element 113 in the optical cavity, or both a saturable absorber and an acousto-optic modulator may be used. The saturable absorber may be a $Cr^{+4}$:YAG crystal. The operation of the modulator may be controlled by an electronic or computer-generated clock signal. Such electronic clock-controlled modulators are readily available. The resultant pulses, which may range in pulse width from 0.1 psec to 10 nsec, raise the pulse power and consequently the conversion process efficiency. The thus-generated 1197 nm laser optical pulses emanate as beam 164 at the output of cavity mirror 161. This beam is expanded by telescope 165, producing the larger beam 166 which passes on to the delivery system 211, schematically represented in FIG. 2. Still referring to FIG. 1, computer system 167, taking programming instructions input 173 from an operator (not indicated), issues control signals 170 and 171. Signal 171 of the control computer enters the pump diode lasers 146 and 128 as signals 149 and 129. These control signals adjust the laser parameters, for example power, pulse rate and start- and stop-times. Signal 170 goes on to simultaneously control the laser pulse delivery system 211 of FIG. 2. Computer 167 also receives signal 174 from pulse delivery system 211 which aids in the control of the treatment process as will be described in the following.

Figure 2:
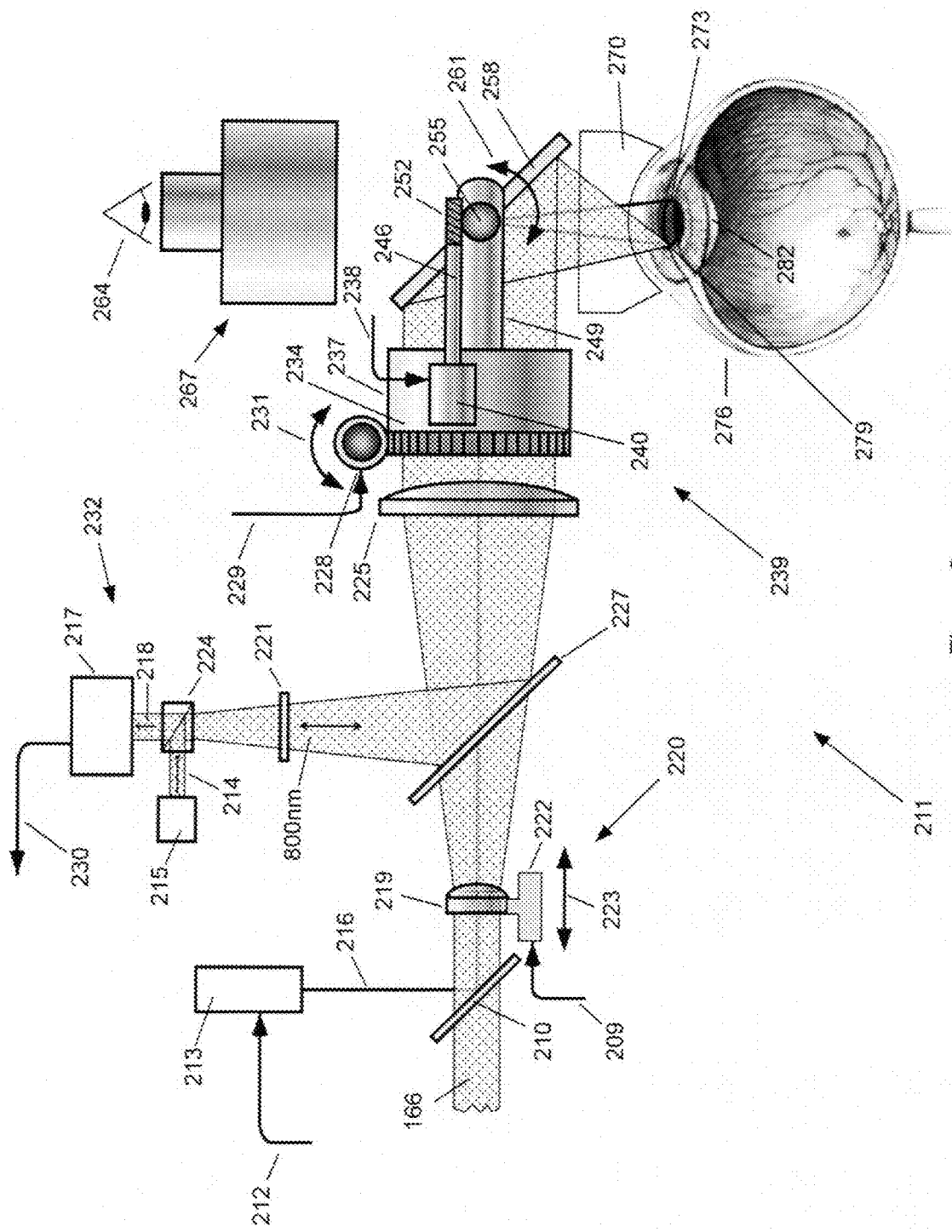
FIG. 2 is a schematic in partial axial section of a delivery system suitable for use in one embodiment of the invention.

Referring now to FIG. 2, laser pulse delivery system 211 is comprised of an aiming low-power visible laser beam source 213, which may be a HeNe 633 nm source, dynamic focusing system 220, eye tracking sensor system 232, dichroic reflectors 210, 227 and 258, beam focusing lenses 219 and 225, rapid two-dimensional beam articulating system 239 and surgery viewing microscope system 267. The operating surgeon may view the target to be treated, as indicated by the eye symbol 264, by means of microscope 267 through dichroic beam splitter 258, which passes the image of the treatment site (the eye of the patient 276 and, in particular, the anterior capsule 273 or posterior capsule, not indicated) of natural lens 282 of eye 276. Optional contact lens 270 may be employed to assist stabilizing and focusing of the delivered treatment beam 166. Element 258 is preferably a dichroic reflector that preferentially reflects 1197 nm laser treatment light pulses and 800 nm eye tracking illumination light and essentially blocks off any laser and near infrared light from reflecting back to the surgeon's eye(s), while passing a clear visible image of the treatment site.

With continued reference to FIG. 2, the function of the delivery system is detailed in terms of its actual use by a surgeon as follows: The first step of the function is initiated while the treatment laser beam 166 is maintained in the off-state. This is the aiming and treatment adjustment step. Aiming beam 216 from alignment laser 213 is co-aligned with the path of the treatment beam 166 by means of dichroic reflector 210 which passes for example 1197 nm but reflects 633 nm. The aiming beam generally passes through the entire optical path and projects a focused point on the target capsule layer. By means of the control signal 173 of FIG. 1, the surgeon adjusts the focus of the aiming beam by means of signal 170 of FIG. 1, part of which is the control signal 209 in FIG. 2, acting on lens positioning mechanism 222, moving lens 219 along dimension 223. The thus moved lens in conjunction with lens 225 establishes a focused point 279 on the lens capsule of eye 276.

With continued reference to FIG. 2, the second step of the function may be to establish eye tracking to secure accurate delivery of the treatment process. This preliminary step is also accomplished by maintaining the treatment laser in the off-state. The principal components of the eye tracking system 232 are an IR illuminator 215, image position sensitive detector system 217, such as are described in the eye tracker disclosed in U.S. Pat. No. 5,345,281, which is hereby incorporated herein by reference, polarizing beam-splitter cube 224 and band pass filter 221. Other eye tracking systems known in industry or that may become available may also be used. The IR source may be an LED emitting IR light at 800 nm. This light beam designated as 214 is polarized and reflected by beam splitter cube 224. The polarized illumination light passes through narrow band pass filter 221, which blocks out any extraneous light, and is reflected by dichroic beam splitter 227, which is transparent to 1197 nm laser light. The polarized IR illumination light is passed through the 2-D articulating system 239 and generally illuminates the iris and pupil of treatment site eye 276. IR illumination that is scattered from the iris of eye 276 creates an optical object with a dark circular center representing the angular position of the eye. This scattered light from the eye is imaged back through the system by means of dichroic reflector 258, lens 225, dichroic reflector 227, band pass filter 221 and beam splitter cube 224 to position sensitive detector system 217. The beam splitter cube 224 on this return path blocks the perpendicular polarized illumination and only passes iris scattered light, thereby enhancing the contrast and creating a dark pupil image on the position sensitive detector 217. Movement of the dark pupil spot at the position sensitive detector represents movement of the patient's eye 276. The position-sensitive detector system produces signal 230, which is communicated to the controlling computer as part of signal 174 in FIG. 1. Signal 230 represents the departure of the pupil from a normal centered fixation position. Based on the values of signal 230, control computer system 167 in FIG. 1 automatically computes compensating control signals designated as 170 in FIG. 1 that are received as signals 229 and 238, acting on actuating motors 228 and 240 in FIG. 2. Motors 228 and 240, by means of the articulating system 239, impart azimuth and elevation deflection relative to the optical axis of dichroic mirror 258, compensating the deviation reported by position sensitive detector system 232. This establishes the process of eye tracking, where the pupil and consequently the lens capsule remains stationary relative to the delivery optical axis.

The detail function of articulating system 239 is as follows. With continued reference to FIG. 2, signal 229 causes motor 228 to produce rotary motion 231, which moves by gear 234 hollow cylinder element 237 about an axis coaxial with the optical axis. This imparts an azimuth motion of the dichroic mirror 258 by means of coupling support element 249. Elevation motion 261 of element 258 is generated by motor 240 (which is also coupled to and moves with hollow cylinder 237) in response to signal 238. The elevation motion of dichroic mirror 258 results from the rotation of coupled axle gear 255 actuated by worm gear 252 connected to motor 238 by axle 246.

Having established the eye tracking function as detailed above, the surgeon next examines the programmed pattern on the lens capsule. To obtain this pattern the surgeon enters commands to the central computer 167 of FIG. 1 to execute a preprogrammed procedure that turns on low-power aiming laser 213 in FIG. 2 by means of the control signal 212, producing beam 216, which projects through the articulating system 239 onto patient's eye 276 as focused point 279 on lens capsule of lens 282 of eye 276. The surgeon observes a focused point steadily fixed on a given point on the capsule or other target in the anterior segment of an eye as a result of the eye tracking process detailed above. The surgeon next examines the preprogrammed loci of exposure points displayed as a ring, ellipse or any general contour of preprogrammed dimensions on the capsule for a capsulorhexis. This is done by a rapid and cyclical motion of articulating system 239 executing a controlled motion of dichroic mirror 258, repeatedly yielding the preprogrammed loci of points on capsule 273. Throughout this process, the eye tracking system may contribute controlling corrections as described above to compensate for eye movement so that the surgeon observes a stable rapidly repeated preprogrammed pattern of the subsequent desired surgical treatment. The surgeon may enter adjustments to the programmed pattern generated by control computer system 167 of FIG. 1.

Once the surgeon is satisfied with the desired treatment pattern he may initiate the exposure with treatment laser beam 166 of FIG. 2. This is done by issuing an appropriate command signal to control computer 167 of FIG. 1. For the exposure process the control computer turns on the laser system 109 for a single or few cycles of the desired pattern as observed in the preliminary preprogrammed loci detailed above.

With the aforementioned computer control signals, highly reliable and reproducible capsulectomies can be accomplished by a reasonably trained surgeon. In other embodiments, an electrical beam-scanning device, such as employing well-known galvanometers, may be used in place of the mechanical beam-scanning device disclosed herein. Either beam-scanning device is preferably adapted to be accommodated in the working distance of the viewing optical system.

The invention described above, therefore, provides an improved surgical instrument and methods for the performance of lenticular capsulectomy.

The laser system of FIG. 1 and the delivery system of FIG. 2 may also be used in other surgical applications in the anterior segment of an eye. In cataract surgery, the laser pulses may be used for photodisintegration of a portion of or all of the interior material of a lens, using methods such as disclosed in WO 2009/039302, which is hereby incorporated by reference herein in its entirety. The wavelength disclosed herein provides safer procedures than provided by the shorter wavelengths of other lasers. Focus depth of the laser beam may be adjusted to cause photodisintegration in a selected pattern in the capsule. The photodisintegration may be used non-invasively. It may be followed by the usual procedure for cataract removal.

There is a great need for techniques to correct or prevent presbyopia. By programming patterns of laser pulses to be applied in x, y and z directions, using the apparatus of FIGS. 1 and 2, all or part of the nucleus or cortex of a lens capsule may be treated with pulses having a selected intensity, preferred wavelengths provided by the apparatus, pulse frequency and width and pre-programmed treatment loci. Such pulses at a preferred frequency can disrupt the bonds between molecules or aggregates in crystalline lens 282. The pulses may be delivered over a very wide frequency range and the most effective frequency or frequencies selected. The pulses cause temperature and volume changes, creating sonic pulses. Such disruption can decrease the rigidity of lens 282 and allow greater accommodation of eye 276.

The laser system of FIG. 1 and the delivery system of FIG. 2 may also be used by the surgeon to form the incision in a cornea during cataract surgery. This step may be taken before or after the capsulorhexis. Beam articulating system 239 (FIG. 2) may be adjusted with respect to eye 276 to allow a pattern to be formed on the cornea of the eye at a selected location, which may be at an angle greater then 75 degrees off the optic axis of the eye. The selected pattern for such incision, which may be circular or elliptical, for example, may be programmed in computer 167. The beam may then be focused at a depth to afford formation of the incision.

Rather than forming an incision in the cornea, the thickness of the cornea may be modified in selected areas using the apparatus of FIGS. 1 and 2. Arcuate cuts may be made in the cornea, for example. Such techniques are well known for correction of astigmatism and other visual deficiencies in an eye. The selected pattern for such treatment of a cornea may be programmed in computer 167.

The laser pulses provided by the apparatus and methods disclosed herein provide several advantages over prior art apparatus and methods. (1) The range of wavelengths is selected to obtain optimum absorption in water and lipids, which means that lower power levels of the laser are required to obtain photo-dielectric breakdown; and (2) the focusing characteristic allows cutting of tissue to occur where the light is focused while using a source that is far below the damage threshold of the retina. All these characteristics are safety mechanisms for use of a laser in anterior segment eye surgery.

It is understood that modifications to the invention may be made as might occur to one skilled in the field of the invention within the scope of the appended claims. All embodiments contemplated hereunder which achieve the objects of the invention have not been shown in complete detail. Other embodiments may be developed without departing from the spirit of the invention or from the scope of the appended claims. Although the present invention has been described with respect to specific details, it is not intended that such details should be regarded as limitations on the scope of the invention, except to the extent that they are included in the accompanying claims.

We claim:

1. A non-invasive capsulectomy instrument, comprising:
a Raman crystal in an optical cavity to shift a laser gain crystal wavelength to a Raman shift-generated wavelength;
a double- or single-end laser gain crystal in the optical cavity to produce the laser gain crystal wavelength;
a device in the optical cavity to obtain a train of pulses of the Raman shift-generated wavelength;
single or dual pump lasers to produce a pump laser radiation;
optical coupling means to convey the pump laser radiation through cavity reflectors into a selected distribution of radiation in the cavity gain crystal;
laser cavity reflector mirrors to resonate the laser gain crystal wavelength simultaneously with the Raman shift-generated wavelength;
a laser pulse delivery system to deliver a train of laser pulses over pre-programmed loci;
an eyetracking system,
a computer system for controlling the adjustable parameters of the pump lasers, parameters associated with the device in the optical cavity to obtain the train of pulses, parameters associated with the eye tracking system and parameters of the delivery system; and
a viewing optical system that allows an operator to view an eye simultaneously with operation of the instrument.

2. The capsulectomy instrument of claim 1 wherein the device in the optical cavity to obtain a train of pulses is a Q-switch modulator or a mode locking modulator.

3. The capsulectomy instrument of claim 1 wherein the device in the optical cavity to obtain a train of pulses is a combination Q-switch modulator and mode locking modulator.

4. The capsulectomy instrument of claim 1 further comprising an intracavity beam-reducing telescope for increasing the irradiance through the Raman crystal.

5. The capsulectomy instrument of claim 1 wherein the Raman crystal comprises a crystal that exhibits Raman conversion gain for producing light at wavelengths in the range from about 1100 nm to about 1300 nm greater than about 20 per cent when acting on the laser gain crystal wavelength.

6. The capsulectomy instrument of claim 1 wherein the Raman crystal is barium nitrate.

7. The capsulectomy instrument of claim 1 wherein the laser gain crystal is a crystal that exhibits laser gain at wavelengths in the range from about 1000 nm to about 1100 nm.

8. The capsulectomy instrument of claim 1 wherein the laser gain crystal is Nd:YAG or Nd:VO$_4$.

9. The capsulectomy instrument of claim 1 wherein the device in the optical cavity to obtain a train of pulses is a saturable absorber for the laser gain crystal wavelength and is minimally absorbing for the Raman shift-generated wavelength.

10. The capsulectomy instrument of claim 9 wherein the saturable absorber is the crystal Cr+4:YAG.

11. The capsulectomy instrument of claim 1 wherein the device in the optical cavity to obtain a train of pulses is an acousto-optic modulator.

12. The capsulectomy instrument of claim 1 wherein the pump lasers are solid state diodes that generate emission in the middle of the absorption band of the laser cavity gain crystal.

13. The capsulectomy instrument of claim 1 wherein the pump lasers are solid state diodes that generate laser emission at 808 nm.

14. The capsulectomy instrument of claim 1 wherein the delivery system includes an aiming laser, beam-combining dichroic reflectors, an eye tracking system, a beam expansion and focusing optics, and a two-dimensional beam articulator.

15. The capsulectomy instrument of claim 1 wherein the parameters of the delivery system controlled by the computer system include the parameters of the aiming laser with beam-combining dichroic reflector, the eye tracking system, the beam expansion and focusing optics, and the two-dimensional beam articulator.

16. The computer automated delivery system of claim 14 wherein the aiming laser is used to designate a pre-treatment pattern on the target tissue.

17. The computer automated laser delivery system of claim 14 wherein the two-dimensional beam articulator is used to both generate a pretreatment pattern and deliver the treatment laser pulses.

18. The computer automated laser delivery system of claim 14 wherein the beam expansion and focusing optics expands and adjusts the focus simultaneously of the Raman shift-generated laser pulses combined with the aiming laser to a focus spot on a target lens capsule.

19. The computer automated delivery system of claim 14 wherein the two-dimensional beam articulator is comprised of a first azimuth angle articulating mechanism, a second elevation angle articulating mechanism and an unobscured dichroic reflector.

20. The computer automated delivery system of claim 14 wherein the beam articulator is an electrical beam scanning device.

21. The computer automated delivery system of claim 14 wherein the dichroic reflector permits the reflection and direction of the treatment Raman shift-generated laser pulses and the viewing optical system without exposing the operator to laser light.

22. The computer automated delivery system of claim 1 wherein the viewing optical system is a slit lamp, operating microscope, or ophthalmoscope.

23. The computer laser delivery system of claim 1 wherein the delivery system is adapted to be accommodated in the working distance of the viewing optical system.

24. A method for forming a capsulectomy in an eye, comprising:
  (a) supplying a capsulectomy instrument comprising
    a Raman crystal in an optical cavity to shift a laser gain crystal wavelength to a Raman shift-generated wavelength;
    a double- or single-end laser gain crystal in the optical cavity to produce the laser gain crystal wavelength;
    a device in the optical cavity to obtain a train of pulses of the Raman shift-generated wavelength;
    single or dual pump lasers to produce a pump laser radiation;
    optical coupling means to convey the pump laser radiation through cavity reflectors into a selected distribution of radiation in the cavity gain crystal;
    laser cavity reflector mirrors to resonate the laser gain crystal wavelength simultaneously with the Raman shift-generated wavelength;
    a laser pulse delivery system to deliver a train of laser pulses over pre-programmed loci;
    an eyetracking system,
    a computer system for controlling the adjustable parameters of the pump lasers, parameters associated with the device in the optical cavity to obtain the train of pulses, parameters associated with the eye tracking system and parameters of the delivery system; and a viewing optical system that allows an operator to view an eye simultaneously with operation of the instrument;
  (b) placing an eye to be treated in the field of the viewing optical system;
  (c) programming the computer system to form a selected pattern for forming the capsulectomy;
  (d) activating an aiming beam and focusing the beam on a lens of the eye;
  (e) activating the eye tracking system,
  (f) operating the delivery system to form a selected pattern of the aiming beam; and
  (g) activating the pump laser or lasers to produce a train of pulses of Raman shift-generated wavelength to treat the portion of the contents of the lens of the eye in the selected pattern.

25. A method for disintegration of a selected portion of the contents of a lens of an eye, comprising:
  (a) supplying a capsulectomy instrument comprising
    a Raman crystal in an optical cavity to shift a laser gain crystal wavelength to a Raman shift-generated wavelength;
    a double- or single-end laser gain crystal in the optical cavity to produce the laser gain crystal wavelength;
    a device in the optical cavity to obtain a train of pulses of the Raman shift-generated wavelength;
    single or dual pump lasers to produce a pump laser radiation;
    optical coupling means to convey the pump laser radiation through cavity reflectors into a selected distribution of radiation in the cavity gain crystal;
    laser cavity reflector mirrors to resonate the laser gain crystal wavelength simultaneously with the Raman shift-generated wavelength;

a laser pulse delivery system to deliver a train of laser pulses over pre-programmed loci;

an eyetracking system, a computer system for controlling the adjustable parameters of the pump lasers, parameters associated with the device in the optical cavity to obtain the train of pulses, parameters associated with the eye tracking system and parameters of the delivery system; and a viewing optical system that allows an operator to view an eye simultaneously with operation of the instrument;

(b) placing the eye to be treated in the field of the viewing optical system;

(c) programming the computer system to form a selected pattern for disintegration of the portion of the contents;

(d) activating an aiming beam and focusing the beam on the selected portion of the contents of the lens of the eye;

(e) activating the eye tracking system;

(f) operating the delivery system to form a selected pattern of the aiming beam; and (g) activating the pump laser or lasers to produce a train of pulses of Raman shift-generated wavelength to treat the portion of the contents of the lens of the eye in the selected pattern.

26. A method for preventing or correcting presbyopia, comprising:

(a) supplying a capsulectomy instrument comprising a Raman crystal in an optical cavity to shift a laser gain crystal wavelength to a Raman shift-generated wavelength;

a double- or single-end laser gain crystal in the optical cavity to produce the laser gain crystal wavelength;

a device in the optical cavity to obtain a train of pulses of the Raman shift-generated wavelength;

single or dual pump lasers to produce a pump laser radiation;

optical coupling means to convey the pump laser radiation through cavity reflectors into a selected distribution of radiation in the cavity gain crystal;

laser cavity reflector mirrors to resonate the laser gain crystal wavelength simultaneously with the Raman shift-generated wavelength;

a laser pulse delivery system to deliver a train of laser pulses over pre-programmed loci;

an eyetracking system, a computer system for controlling the adjustable parameters of the pump lasers, parameters associated with the device in the optical cavity to obtain the train of pulses, parameters associated with the eye tracking system and parameters of the delivery system; and a viewing optical system that allows an operator to view an eye simultaneously with operation of the instrument;

(b) placing the eye to be treated in the field of the viewing optical system;

(c) programming the computer system to form a selected pattern for applying laser pulses;

(d) activating an aiming beam and focusing the beam on a portion of the contents of the lens of the eye;

(e) activating the eye tracking system, (f) operating the delivery system to form a selected pattern of the aiming beam; and (g) activating the pump laser or lasers to produce a train of pulses of Raman shift-generated wavelength and treating the portion of the contents of the lens of the eye in the selected pattern.

27. A method for forming an incision in a cornea of an eye at a selected location, comprising:

(a) supplying a capsulectomy instrument comprising a Raman crystal in an optical cavity to shift a laser gain crystal wavelength to a Raman shift-generated wavelength;

a double- or single-end laser gain crystal in the optical cavity to produce the laser gain crystal wavelength;

a device in the optical cavity to obtain a train of pulses of the Raman shift-generated wavelength;

single or dual pump lasers to produce a pump laser radiation;

optical coupling means to convey the pump laser radiation through cavity reflectors into a selected distribution of radiation in the cavity gain crystal;

laser cavity reflector mirrors to resonate the laser gain crystal wavelength simultaneously with the Raman shift-generated wavelength;

a laser pulse delivery system to deliver a train of laser pulses over pre-programmed loci;

an eyetracking system, a computer system for controlling the adjustable parameters of the pump lasers, parameters associated with the device in the optical cavity to obtain the train of pulses, parameters associated with the eye tracking system and parameters of the delivery system; and a viewing optical system that allows an operator to view an eye simultaneously with operation of the instrument;

(b) placing the eye to be treated in the field of the viewing optical system;

(c) programming the computer system to form a selected pattern for the incision at the selected location;

(d) activating an aiming beam and focusing the beam on the cornea at the selected location;

(e) activating the eye tracking system;

(f) operating the delivery system to form the selected pattern of the aiming beam; and (g) activating the pump laser or lasers to produce a train of pulses of Raman shift-generated wavelength and forming the incision.

28. A method for correcting visual deficiencies of an eye, comprising:

(a) supplying a capsulectomy instrument comprising a Raman crystal in an optical cavity to shift a laser gain crystal wavelength to a Raman shift-generated wavelength;

a double- or single-end laser gain crystal in the optical cavity to produce the laser gain crystal wavelength;

a device in the optical cavity to obtain a train of pulses of the Raman shift-generated wavelength;

single or dual pump lasers to produce a pump laser radiation;

optical coupling means to convey the pump laser radiation through cavity reflectors into a selected distribution of radiation in the cavity gain crystal;

laser cavity reflector mirrors to resonate the laser gain crystal wavelength simultaneously with the Raman shift-generated wavelength;

a laser pulse delivery system to deliver a train of laser pulses over pre-programmed loci;

an eyetracking system, a computer system for controlling the adjustable parameters of the pump lasers, parameters associated with the device in the optical cavity to obtain the train of pulses, parameters associated with the eye tracking system and parameters of the delivery system; and a viewing optical system that allows an operator to view an eye simultaneously with operation of the instrument;
(b) placing the eye to be treated in the field of the viewing optical system;
(c) programming the computer system to form a selected pattern at the selected location on a portion of the cornea of the eye;
(d) activating an aiming beam and focusing the beam on the portion of the cornea at the selected location;
(e) activating the eye tracking system;
(f) operating the delivery system to form the selected pattern of the aiming beam; and
(g) activating the pump laser or lasers to produce a train of pulses of Raman shift-generated wavelength and correcting the visual deficiencies.

* * * * *